United States Patent
Obot et al.

(10) Patent No.: US 11,959,016 B2
(45) Date of Patent: Apr. 16, 2024

(54) INHIBITING CORROSION IN GAS WELLS

(71) Applicants: Saudi Arabian Oil Company, Dhahran (SA); King Fahd University of Petroleum & Minerals, Dhahran (SA)

(72) Inventors: Ime Bassey Obot, Dhahran (SA); Mumtaz A. Quraishi, Dhahran (SA); Ahmad A. Sorour, Dhahran (SA); Tao Chen, Dhahran (SA); Qiwei Wang, Dhahran (SA); Mohammed A. Bataweel, Dhahran (SA); Bader Ghazi Al-Harbi, Dammam (SA)

(73) Assignees: Saudi Arabian Oil Company, Dhahran (SA); King Fahd University of Petroleum & Minerals, Dhahran (SA)

( * ) Notice: Subject to any disclaimer, the term of this patent is extended or adjusted under 35 U.S.C. 154(b) by 0 days.

(21) Appl. No.: 17/347,952

(22) Filed: Jun. 15, 2021

(65) Prior Publication Data

US 2022/0403224 A1    Dec. 22, 2022

(51) Int. Cl.
*C23F 11/14* (2006.01)
*C07D 471/14* (2006.01)
*C09K 8/54* (2006.01)

(52) U.S. Cl.
CPC .............. *C09K 8/54* (2013.01); *C07D 471/14* (2013.01); *C23F 11/146* (2013.01); *C23F 11/149* (2013.01); *C09K 2208/32* (2013.01)

(58) Field of Classification Search
CPC ....... C23F 11/14; C23F 11/146; C23F 11/149; C09K 8/54; C09K 2208/32; C02F 5/10;
(Continued)

(56) References Cited

U.S. PATENT DOCUMENTS 6,586,120 B2 *  7/2003  Tao ................. C09B 57/008
                                                548/440
6,734,190 B2 *  5/2004  Green .............. C07D 471/14
                                                546/82
(Continued)

FOREIGN PATENT DOCUMENTS

BE         616472 A  * 10/1962
DE       294481 A5  * 10/1991
(Continued)

OTHER PUBLICATIONS

Balasubramaniam et al. ("Blue light-emitting diodes based on dipyrazolopyridine derivatives," Chem. Mater., 2000, 12, 2788-2793) (Year: 2000).*

(Continued)

*Primary Examiner* — Matthew R Diaz
(74) *Attorney, Agent, or Firm* — Fish & Richardson P.C.

(57) ABSTRACT

A composition for inhibiting corrosion in gas wells includes a pyrazolopyridine derivative. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety. The composition can be flowed into a wellbore formed in a subterranean formation, thereby inhibiting corrosion in the wellbore.

4 Claims, 8 Drawing Sheets

(58) Field of Classification Search
CPC ....... C02F 5/12; C07D 471/04; C07D 471/14; C07D 471/22

See application file for complete search history.

(56) References Cited

U.S. PATENT DOCUMENTS

| | | | |
|---|---|---|---|
| 6,900,223 B2 * | 5/2005 | Green | C07D 471/14 514/252.04 |
| 7,057,050 B2 | 6/2006 | Meyer et al. | |
| 7,465,747 B2 * | 12/2008 | Matsumoto | C07D 401/14 514/183 |
| 8,618,027 B2 | 12/2013 | Meyer et al. | |
| 2015/0069301 A1 | 3/2015 | Sun et al. | |
| 2023/0002666 A1 | 1/2023 | Obot et al. | |

FOREIGN PATENT DOCUMENTS

| | | | | |
|---|---|---|---|---|
| EP | 1333108 | 9/2006 | | |
| WO | WO-9828296 A1 * | 7/1998 | ............ | C07D 471/04 |
| WO | WO-2021101227 A1 * | 5/2021 | ......... | C11D 11/0047 |

OTHER PUBLICATIONS

Tao et al. ("Dipyrazolopyridine derivatives as bright blue electroluminescent materials," Appl. Phys. Lett. 77, 933, 2000) (Year: 2000).*

Lipson et al. ("Heterocyclizations of 5-methylpyrazol-3-amine with unsaturated arylaliphatic carboxylic acid derivatives," Russian Journal of Organic Chemistry, vol. 42, No. 7, 1022-1027, 2006) (Year: 2006).*

Ma et al. ("Synthesis and optical properties of bispyrazolopyridine derivatives," Dyes and Pigments 181, 2020, 108569) (Year: 2020).*

Kido et al. ("White light-emitting organic electroluminescent devices using the poly(N-vinylcarbazole) emitter layer doped with three fluorescent dyes," Appl. Phys. Lett. 64, 815-817, 1994) (Year: 1994).*

El Mhammedi et al. ("Investigation of the inhibitive effect of pyrazolo [3,4-b] pyridine on corrosion of stainless steel in 1 M HCI solutions", Leonardo Electronic Journal of Practices and Technologies, 11, 2007, 37-46) (Year: 2007).*

Fekry et al. ("Corrosion inhibition of mild steel in acidic media using newly synthesized heterocyclic organic molecules", International Journal of Hydrogen Energy 35, 2010, 7641-7651) (Year: 2010).*

Dandia et al. ("Ultrasound-assisted synthesis of pyrazolo[3,4-b]pyridines as potential corrosion inhibitors for mild steel in 1.0 M HCI", ACS Sustainable Chem. Eng. 2013, 1, 1303-1310) (Year: 2013).*

Sundheer ("The corrosion inhibition effect of aryl pyrazolo pyridines on copper in hydrochloric acid system: Computational and electrochemical studies", RSC Advances, 5(52), 2015, 41923-51933) (Year: 2015).*

Mousa ("Synthesis, characterization and corrosion inhibition of pyrazolo[1,5-a][1,8]naphthyridine, pyrazolo[1,5-a]pyridine and pyrazolo[1,5-a]pyrimidine derivatives, quantum chemical approach", International Journal of Chemical Studies 2017, 5(3), 290-296) (Year: 2017).*

Yadav et al., "Corrosion inhibition performance of pyranopyrazole derivatives for mild steel in HCI solution: Gravimetric, electrochemical and DFT studies," Journal of Molecular Liquids, 2016, 216:78-86, 9 pages.

Astm G3, "Standard Practice and Conventions Applicable to Electrochemical Measurements in Corrosion Testing," ASTM International, Reapproved 2014, 9 pages.

Azzouzi et al., "Inhibition effect of 1,1'-(pyridine-2,6-dihylbis(methylene))bis(5-methyl-1-Hpyrazole-3-carboxylic acid) on the corrosion of mild steel in 1 M HCL. Part A: Experimental study," Int. J. Corros. Scale Inhibi., 2017, 6(4):463-475, 13 pages.

Dohare et al., "Pyranpyrazole Derivatives as Novel Corrosion Inhibitors for Mild Steel Useful for Industrial Pickling Process: Experimental and Quantum Chemical Study," Journal of Industrial Engineering Chemistry, 2017, 52:197-210, 14 pages.

El Hajjaji et al., "Corrosion Resistance of Mild Steel Coated with Organic Material Containing Pyrazol Moiety," Coatings, 2018, 8:330, 17 pages.

El-Lateef et al., "Corrosion Protection of Steel Pipelines Against $CO_2$ Corrosion—A Review," Chemistry Journal, 2012, 2(2):52-63, 13 pages.

Herrag et al., "Pyrazole Derivatives as Corrosion Inhibitors for Steel in Hydrochloric Acid," Portualiae Electrochimica Acta, 2008, 26:211-220, 10 pages.

Hoshowski et al., "The development of novel corrosion inhibitors for high temperature sour gas environments," NACE International Paper No. C-2020-14591, 2020, 9 pages.

Kahyarian et al., "CO2 corrosion of mild steel," Trends in Oil and Gas Corrosion Research and Technologies, Elsevier, 2017, 42 pages.

Liu et al., "Understanding thermal stability and inhibition effectiveness of corrosion inhibitors at high temperatures," NACE International Paper No. 7535, 2016, 11 pages.

Mazumder et al., "Design and synthesis of a novel class of inhibitors for mild steel corrosion in acidic and carbon dioxide-saturated saline media," Corros. Sci., 2014, 87:187-198, 12 pages.

Singh et al., "Bispyranopyrazoles as Green Corrosion Inhibitors for Mild Steel in Hydrochloric Acide: Experimental and Theoretical Approach," ASC Omega, 2018, 3:11151-11162, 12 pages.

Usman et al., "Carbon dioxide corrosion inhibitors: A review," Arab. J. Sci. Eng., 2017, 23 pages.

Yadav et al., "Electrochemical investigation of Substituted Pyranopyrazoles Adsorption on Mild Steel in Acid Solution," Industrial & Engineering Chemistry Research (I&EC Research), 2012, 51:8194-8210, 17 pages.

* cited by examiner

INHIBITING CORROSION IN GAS WELLS

TECHNICAL FIELD

This disclosure relates to inhibiting corrosion in gas wells.

BACKGROUND

Corrosion can occur in oil and gas processing equipment and piping. Corrosion can occur due to factors such as temperature, the presence of carbon dioxide, the presence of hydrogen sulfide, the presence of electrolytes, and flow conditions. Corrosion can be detrimental if left untreated. For example, untreated corrosion can result in an asset becoming inefficient, unreliable, and in some cases, unsafe. A common solution is to use corrosion inhibitor, which can form a protective barrier against corrosive attack.

SUMMARY

This disclosure describes technologies relating to inhibiting corrosion in gas wells, and more specifically, inhibiting high temperature carbon dioxide corrosion in gas wells. Certain aspects of the subject matter can be implemented as a composition for inhibiting corrosion in gas wells. The composition includes a pyrazolopyridine derivative. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety.

This, and other aspects, can include one or more of the following features. In some implementations, the pyrazolopyridine derivative has a concentration in the composition in a range of from 100 parts per million (ppm) to 10,000 ppm. In some implementations, the phenyl moiety includes an $R_1$ group selected from the group consisting of a methoxy group, a carboxyl group, an aromatic amide group, a thiol group, a nitrile group, an azo group, a pyridyl group, a bromophenyl group, and a sulfonic acid group. In some implementations, the $R_1$ group includes methoxy, mercapto, pyridyl, (bromomethyl)pyridyl, or pyridine-2-aldoxime. In some implementations, the first pyrazole moiety includes an $R_2$ group selected from the group consisting of an alkyl group, a thiol group, a carboxyl group, an aromatic carbonyl group, a hydroxyl group, a methyl amino group, an amide group, and an ester group. In some implementations, the second pyrazole moiety includes an $R_3$ group selected from the group consisting of an alkyl group, an amide group, an amino group, a thiol group, a hydroxyl group, an ester group, and a carboxyl group.

Certain aspects of the subject matter can be implemented as a method. A composition is flowed into a wellbore formed in a subterranean formation, thereby inhibiting corrosion in the wellbore. The composition includes a pyrazolopyridine derivative. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety. A hydrocarbon is produced from the subterranean formation via the wellbore.

This, and other aspects, can include one or more of the following features. In some implementations, the pyrazolopyridine derivative has a concentration in the composition in a range of from 100 parts per million (ppm) to 10,000 ppm. In some implementations, the phenyl moiety includes an $R_1$ group selected from the group consisting of a methoxy group, a carboxyl group, an aromatic amide group, a thiol group, a nitrile group, an azo group, a pyridyl group, a bromophenyl group, and a sulfonic acid group. In some implementations, the $R_1$ group includes methoxy, mercapto, pyridyl, (bromomethyl)pyridyl, or pyridine-2-aldoxime. In some implementations, the first pyrazole moiety includes an $R_2$ group selected from the group consisting of an alkyl group, a thiol group, a carboxyl group, an aromatic carbonyl group, a hydroxyl group, a methyl amino group, an amide group, and an ester group. In some implementations, the second pyrazole moiety includes an $R_3$ group selected from the group consisting of an alkyl group, an amide group, an amino group, a thiol group, a hydroxyl group, an ester group, and a carboxyl group.

Certain aspects of the subject matter can be implemented as a method for producing a corrosion inhibitor for gas wells. Hydrazine hydrate and ethyl acetoacetate are mixed in ethanol to form a first mixture. The first mixture is exposed to ultrasound irradiation. An aldehyde and ammonium acetate are added to the first mixture to form a second mixture. The second mixture is exposed to ultrasound irradiation. Water is added to the second mixture to form a third mixture. The third mixture is exposed to ultrasound irradiation to form a precipitate. The precipitate is separated from the third mixture. The precipitate is crystallized using ethanol to form the corrosion inhibitor. The corrosion inhibitor includes a pyrazolopyridine derivative. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety.

This, and other aspects, can include one or more of the following features. In some implementations, the aldehyde is 4-methoxy benzaldehyde. In some implementations, the first mixture is exposed to ultrasound irradiation at room temperature for about 10 minutes. In some implementations, the second mixture is exposed to ultrasound irradiation at a temperature of about 50 degrees Celsius (° C.) for at least 2 hours. In some implementations, the third mixture is exposed to ultrasound irradiation at room temperature for about 15 minutes. In some implementations, the phenyl moiety includes an $R_1$ group selected from the group consisting of a methoxy group, a carboxyl group, an aromatic amide group, a thiol group, a nitrile group, an azo group, a pyridyl group, a bromophenyl group, and a sulfonic acid group. In some implementations, the $R_1$ group includes methoxy, mercapto, pyridyl, (bromomethyl)pyridyl, or pyridine-2-aldoxime. In some implementations, the first pyrazole moiety includes an $R_2$ group selected from the group consisting of an alkyl group, a thiol group, a carboxyl group, an aromatic carbonyl group, a hydroxyl group, a methyl amino group, an amide group, and an ester group. In some implementations, the second pyrazole moiety includes an $R_3$ group selected from the group consisting of an alkyl group, an amide group, an amino group, a thiol group, a hydroxyl group, an ester group, and a carboxyl group.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

Figure 1:
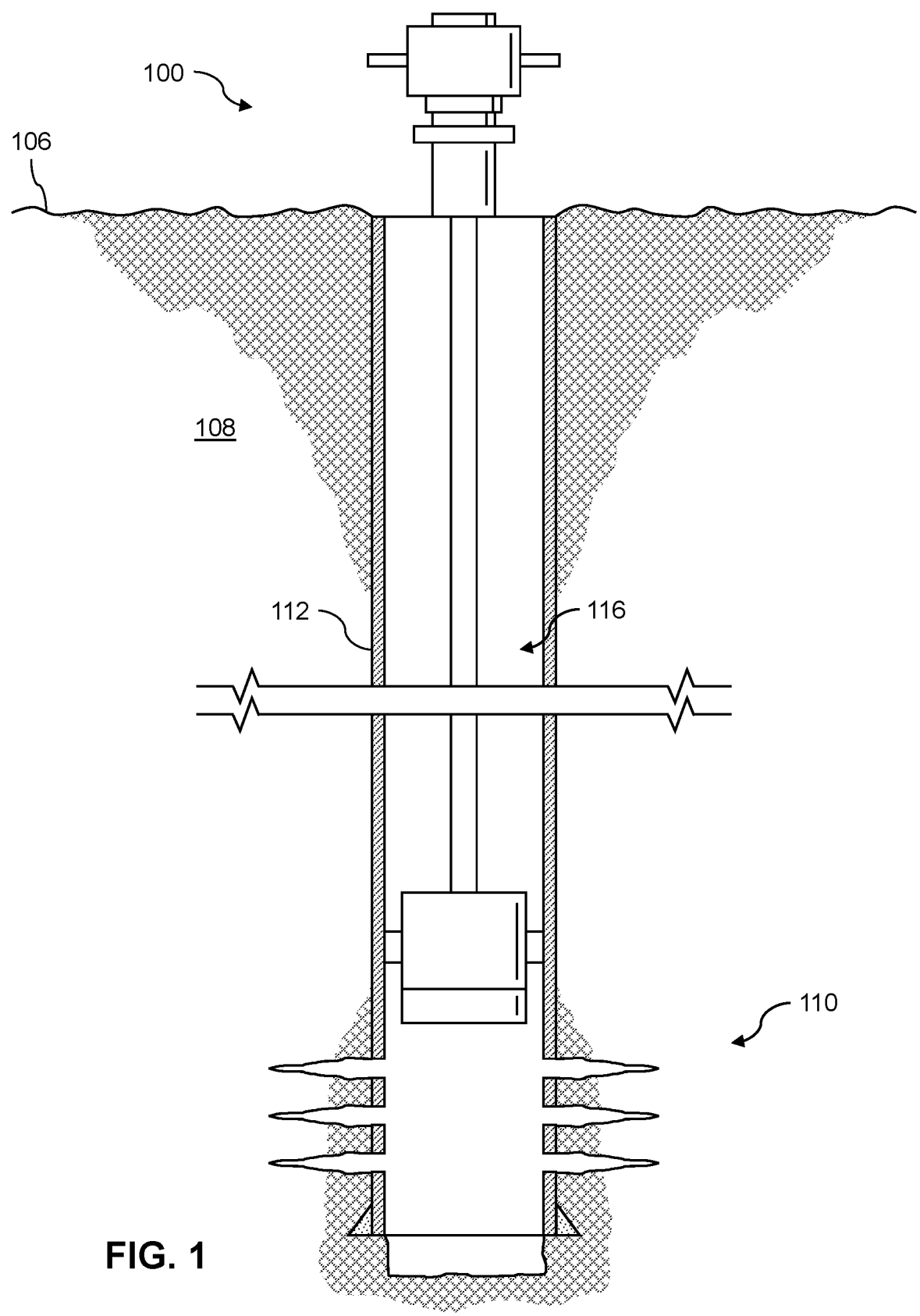
FIG. 1 is a schematic diagram of an example well.

FIG. 1 depicts an example well 100 constructed in accordance with the concepts herein. The well 100 extends from the surface 106 through the Earth 108 to one more subterranean zones of interest 110 (one shown). The well 100 enables access to the subterranean zones of interest 110 to allow recovery (that is, production) of fluids to the surface 106 (represented by flow arrows in FIG. 1) and, in some implementations, additionally or alternatively allows fluids to be placed in the Earth 108. In some implementations, the subterranean zone 110 is a formation within the Earth 108 defining a reservoir, but in other instances, the zone 110 can be multiple formations or a portion of a formation. The subterranean zone can include, for example, a formation, a portion of a formation, or multiple formations in a hydrocarbon-bearing reservoir from which recovery operations can be practiced to recover trapped hydrocarbons. In some implementations, the subterranean zone includes an underground formation of naturally fractured or porous rock containing hydrocarbons (for example, oil, gas, or both). In some implementations, the well can intersect other types of formations, including reservoirs that are not naturally fractured. For simplicity's sake, the well 100 is shown as a vertical well, but in other instances, the well 100 can be a deviated well with a wellbore deviated from vertical (for example, horizontal or slanted), the well 100 can include multiple bores forming a multilateral well (that is, a well having multiple lateral wells branching off another well or wells), or both.

In some implementations, the well 100 is a gas well that is used in producing hydrocarbon gas (such as natural gas) from the subterranean zones of interest 110 to the surface 106. While termed a "gas well," the well need not produce only dry gas, and may incidentally or in much smaller quantities, produce liquid including oil, water, or both. In some implementations, the well 100 is an oil well that is used in producing hydrocarbon liquid (such as crude oil) from the subterranean zones of interest 110 to the surface 106. While termed an "oil well," the well not need produce only hydrocarbon liquid, and may incidentally or in much smaller quantities, produce gas, water, or both. In some implementations, the production from the well 100 can be multiphase in any ratio. In some implementations, the production from the well 100 can produce mostly or entirely liquid at certain times and mostly or entirely gas at other times. For example, in certain types of wells it is common to produce water for a period of time to gain access to the gas in the subterranean zone. The concepts herein, though, are not limited in applicability to gas wells, oil wells, or even production wells, and could be used in wells for producing other gas or liquid resources or could be used in injection wells, disposal wells, or other types of wells used in placing fluids into the Earth.

The wellbore of the well 100 is typically, although not necessarily, cylindrical. All or a portion of the wellbore is lined with a tubing, such as casing 112. The casing 112 connects with a wellhead at the surface 106 and extends downhole into the wellbore. The wellhead defines an attachment point for other equipment to be attached to the well 100. For example, FIG. 1 shows well 100 being produced with a Christmas tree attached to the wellhead. The Christmas tree includes valves used to regulate flow into or out of the well 100. The casing 112 operates to isolate the bore of the well 100, defined in the cased portion of the well 100 by the inner bore 116 of the casing 112, from the surrounding Earth 108. The casing 112 can be formed of a single continuous tubing or multiple lengths of tubing joined (for example, threadedly) end-to-end. In FIG. 1, the casing 112 is perforated in the subterranean zone of interest 110 to allow fluid communication between the subterranean zone of interest 110 and the bore 116 of the casing 112. In some implementations, the casing 112 is omitted or ceases in the region of the subterranean zone of interest 110. This portion of the well 100 without casing is often referred to as "open hole."

A composition including a corrosion inhibitor, as described in this disclosure, can be flowed into the wellbore of the well 100 to inhibit corrosion in the wellbore. In particular, the composition including the corrosion inhibitor described in this disclosure can be flowed into the wellbore of the well 100 to inhibit high temperature carbon dioxide corrosion. The composition includes a pyrazolopyridine derivative. The pyrazolopyridine derivative is the corrosion inhibitor. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety. In some implementations, the pyrazolopyridine derivative (corrosion inhibitor) has a concentration in the composition in a range of from 100 parts per million (ppm) to 10,000 ppm.

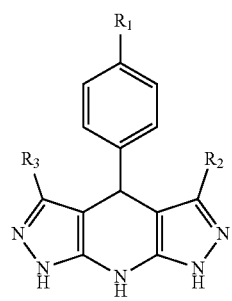

In some implementations, the phenyl moiety includes an $R_1$ group selected from the group consisting of a methoxy group (—OCH$_3$), a carboxyl group (—COOH), an aromatic amide group, a thiol group (—SH), a nitrile group (—CN), an azo group (—NNR', where R' can be aryl or alkyl), a pyridyl group, a bromophenyl group, and a sulfonic acid group (—SO$_3$H). In some implementations, the $R_1$ group includes methoxy, mercapto, pyridyl, (bromomethyl) pyridyl, or pyridine-2-aldoxime.

In some implementations, the first pyrazole moiety includes an $R_2$ group selected from the group consisting of an alkyl group, a thiol group, a carboxyl group, an aromatic carbonyl group, a hydroxyl group (—OH), a methyl amino group, an amide group, and an ester group. In some implementations, the second pyrazole moiety includes an $R_3$ group selected from the group consisting of an alkyl group, an amide group, an amino group (—NH$_2$), a thiol group, a hydroxyl group, an ester group, and a carboxyl group. In some implementations, the $R_2$ group and the $R_3$ group are the same. In some implementations, the $R_2$ group and the $R_3$ group are different.

The subject matter described in this disclosure can be implemented in particular implementations, so as to realize one or more of the following advantages. The pyrazolopyridine derivative (corrosion inhibitor) can be used to mitigate and/or eliminate corrosion in sweet gas and oil fields, and especially for high temperature applications. Mitigating and/or eliminating corrosion using the pyrazolopyridine derivative can extend service life of tubings (for example, completion tubings) in a well. The corrosion inhibitor (pyrazolopyridine derivative) described in this disclosure is capable of maintaining its corrosion inhibiting efficiency at temperatures greater than 100 degrees Celsius (° C.). The corrosion inhibitor (pyrazolopyridine derivative) described in this disclosure can protect steel at temperatures of up to 130° C.

Figure 2:
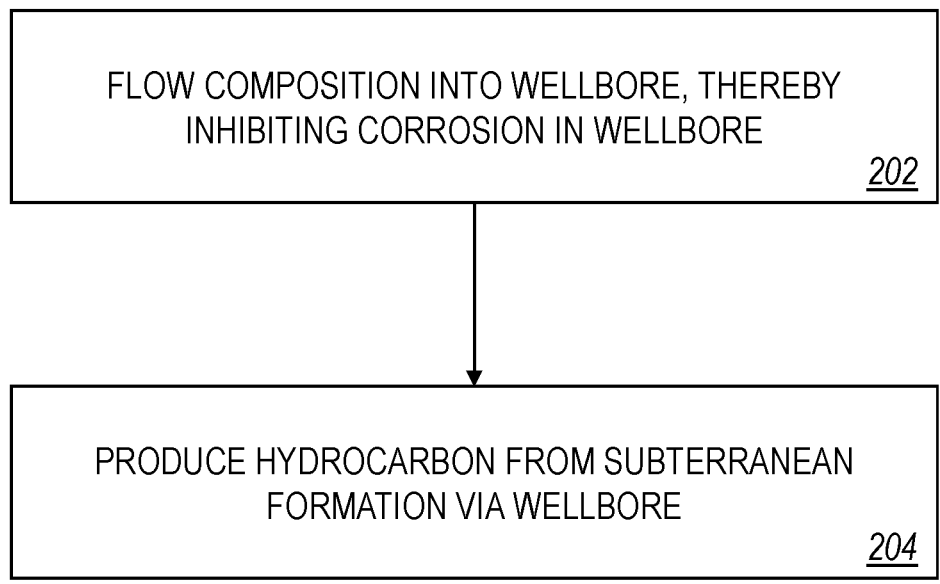
FIG. 2 is a method for inhibiting corrosion in the well of FIG. 1.

FIG. 2 is a method 200 for inhibiting corrosion in a well, for example, the well 100 of FIG. 1. At step 202, a composition is flowed into a wellbore formed in a subterranean formation, such as the wellbore of well 100. By flowing the composition into the wellbore at step 202, corrosion is inhibited in the wellbore. As mentioned previously, the composition includes a pyrazolopyridine derivative, which is the corrosion inhibitor. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety. In some implementations, the composition is flowed into the wellbore in batches (for example, batch treatment) at step 202. In some implementations, the composition is flowed into the wellbore continuously (for example, continuous injection) at step 202. At step 204, a hydrocarbon (for example, a hydrocarbon gas, a hydrocarbon liquid, or a combination of both) is produced from the subterranean formation via the wellbore of well 100.

Figure 3:
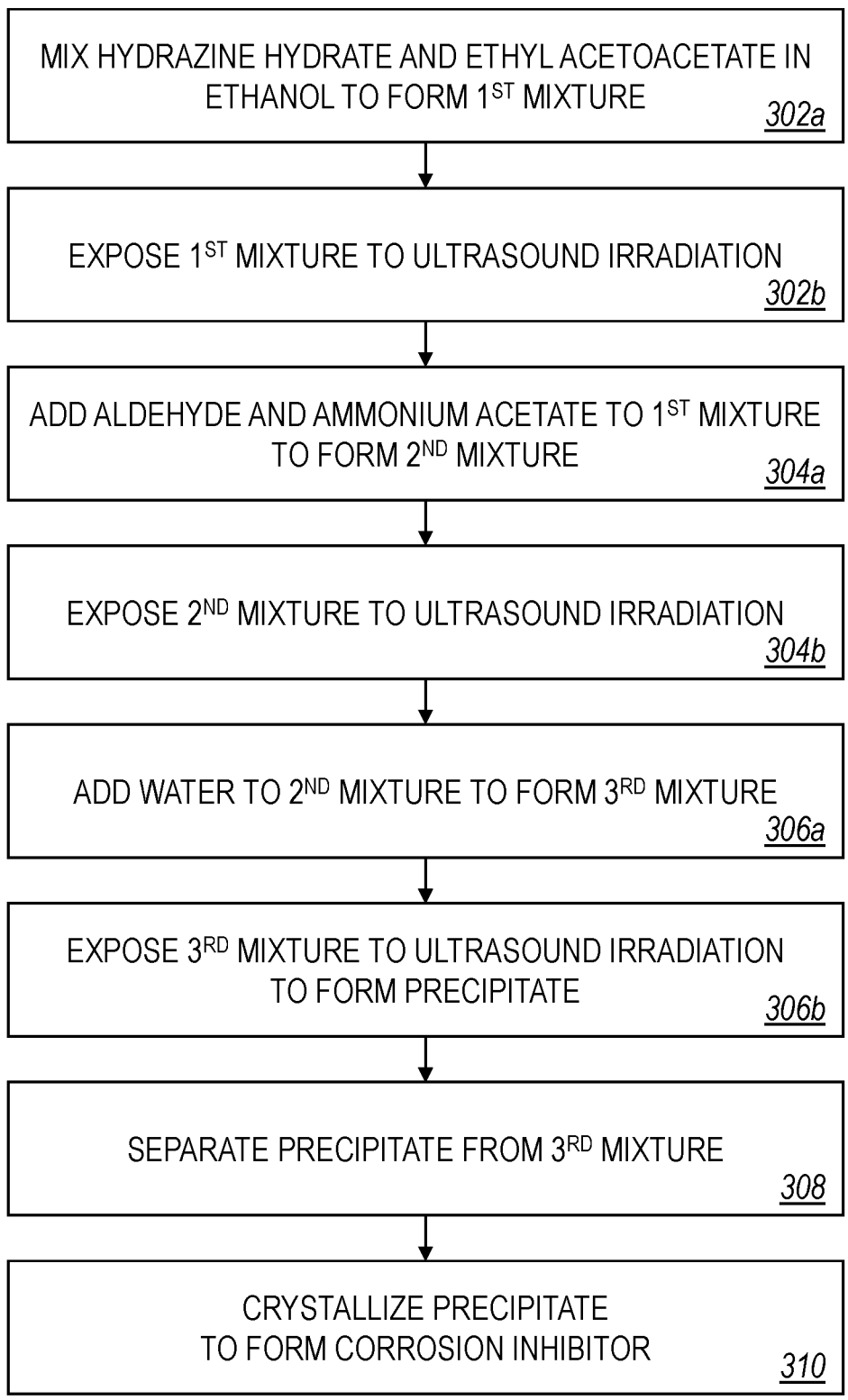
FIG. 3 is a method for producing a corrosion inhibitor that can be used in the well of FIG. 1.

FIG. 3 is a method 300 for producing the corrosion inhibitor (pyrazolopyridine derivative) that can be used in the well 100 of FIG. 1. At step 302a, hydrazine hydrate and ethyl acetoacetate is mixed in ethanol to form a first mixture. At step 302b, the first mixture is exposed to ultrasound irradiation. In some implementations, the first mixture is exposed to ultrasound irradiation at room temperature (for example, about 20° C.) for about 10 minutes at step 302b.

At step 304a, an aldehyde and ammonium acetate is added to the first mixture to form a second mixture. In some implementations, the aldehyde is 4-methoxy benzaldehyde. At step 304b, the second mixture is exposed to ultrasound irradiation. In some implementations, the second mixture is exposed to ultrasound irradiation at a temperature of about 50° C. for at least 2 hours at step 304b.

At step 306a, water is added to the second mixture to form a third mixture. At step 306b, the third mixture is exposed to ultrasound irradiation to form a precipitate. In some implementations, the third mixture is exposed to ultrasound irradiation at room temperature for about 15 minutes at step 306b.

At step 308, the precipitate is separated from the third mixture. For example, the precipitate is filtered from the third mixture at step 308.

At step 310, the precipitate is crystallized using ethanol to form the corrosion inhibitor. The corrosion inhibitor includes a pyrazolopyridine derivative. The pyrazolopyridine derivative includes a pyridyl moiety, a first pyrazole moiety, a second pyrazole moiety, and a phenyl moiety. The first pyrazole moiety is bound to the pyridyl moiety. The second pyrazole moiety is bound to the pyridyl moiety. The phenyl moiety is bound to the pyridyl moiety. In some implementations, the precipitate is washed with water and then dried and crystallized using ethanol at step 310.

Example

Hydrazine hydrate (2.0 millimoles (mmol)) and ethyl acetoacetate (2.0 mmol) was mixed in 15 milliliters (mL) of ethanol to form a first mixture (step 302a). The first mixture was irradiated by an ultrasonicator for 10 minutes at room temperature (step 302b). 4-methoxy aldehyde (1.0 mmol) and ammonium acetate (1.0 mmol) was added to the first mixture to form a second mixture (step 304a). The second mixture was irradiated by the ultrasonicator for 2.5 hours at 50° C. at a sonication power of 450 Watts (W) (step 304b). The extent of reaction completion was monitored. The second mixture was cooled to room temperature. Water (10 mL) was added to the second mixture to form a third mixture (step 306a). The third mixture was irradiated by the ultrasonicator for 15 minutes at room temperature (step 306b). The precipitated product was filtered from the third mixture (step 308). The precipitated product was washed with water, dried with ethanol, and crystallized from ethanol (step 310). The yield was 96%. The melting point of the crystallized product (pyrazolopyridine derivative, which is the corrosion inhibitor) was 206° C. The structural characterization of the synthesized pyrazolopyridine derivative (corrosion inhibitor) was performed using Fourier-transform infrared (FTIR) and nuclear magnetic resonance (NMR) spectroscopy (shown in FIGS. 4, 5, and 6). The thermal stability of the synthesized pyrazolopyridine derivative (corrosion inhibitor) was studied using thermal gravimetric analysis (TGA) (shown in FIG. 7).

Figure 4:
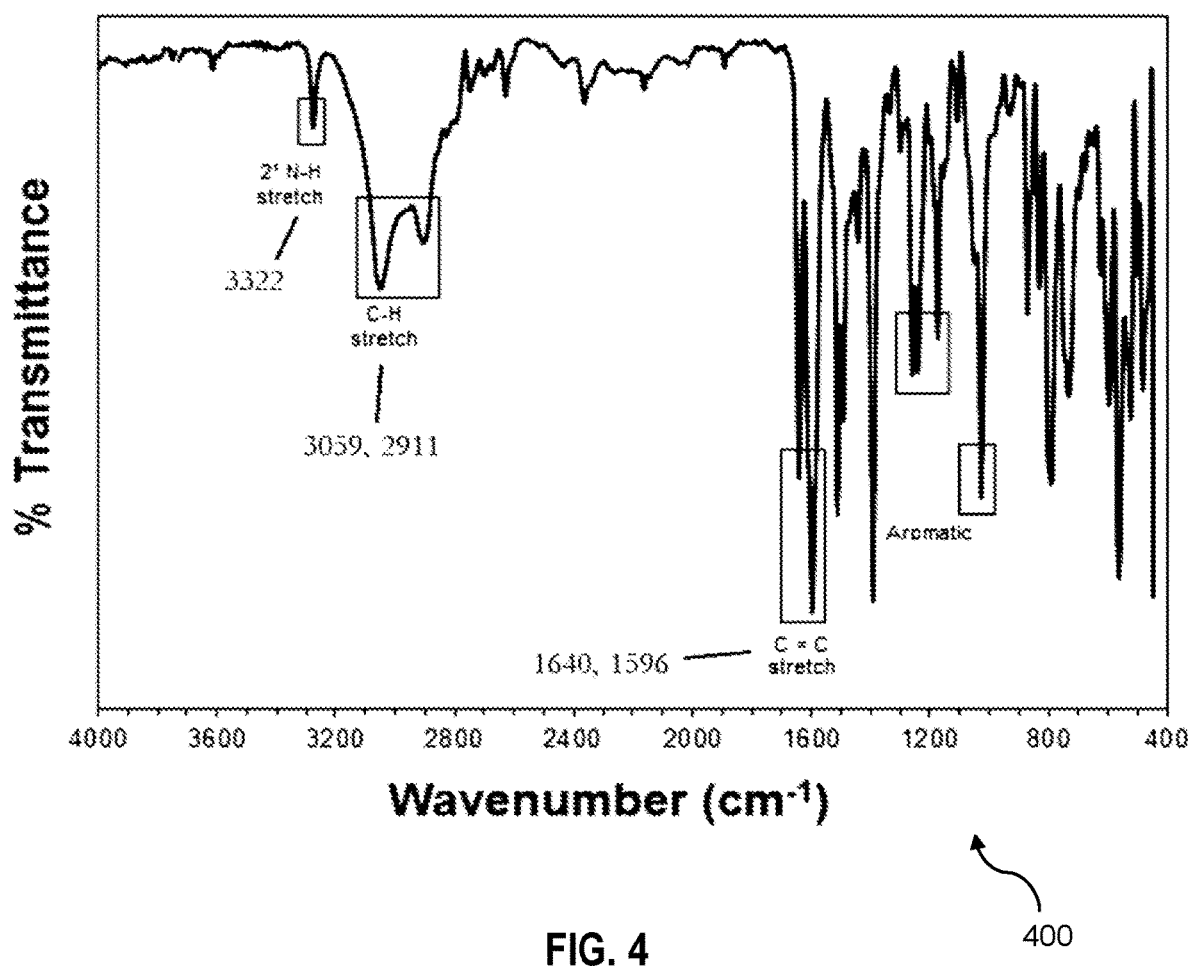
FIG. 4 is a Fourier-transform infrared spectroscopy (FTIR) spectrum of an example corrosion inhibitor.

FIG. 4 is an FTIR spectrum 400 of the pyrazolopyridine derivative (corrosion inhibitor). The characteristic bands and the values of the corresponding wave number are indicated in FIG. 4 and are as follows: $v_{max}$. (KBr) 3322 (NH stretching); 3059, 2911 (CH stretching); 1640, 1596 (C=C stretching); 1511, 1492, 1439, 1391, 1259, 1242, 1201 (aromatic stretching); 1026 (aromatic deform); 870, 833, 791, and 731 cm$^{-1}$.

Figure 5:
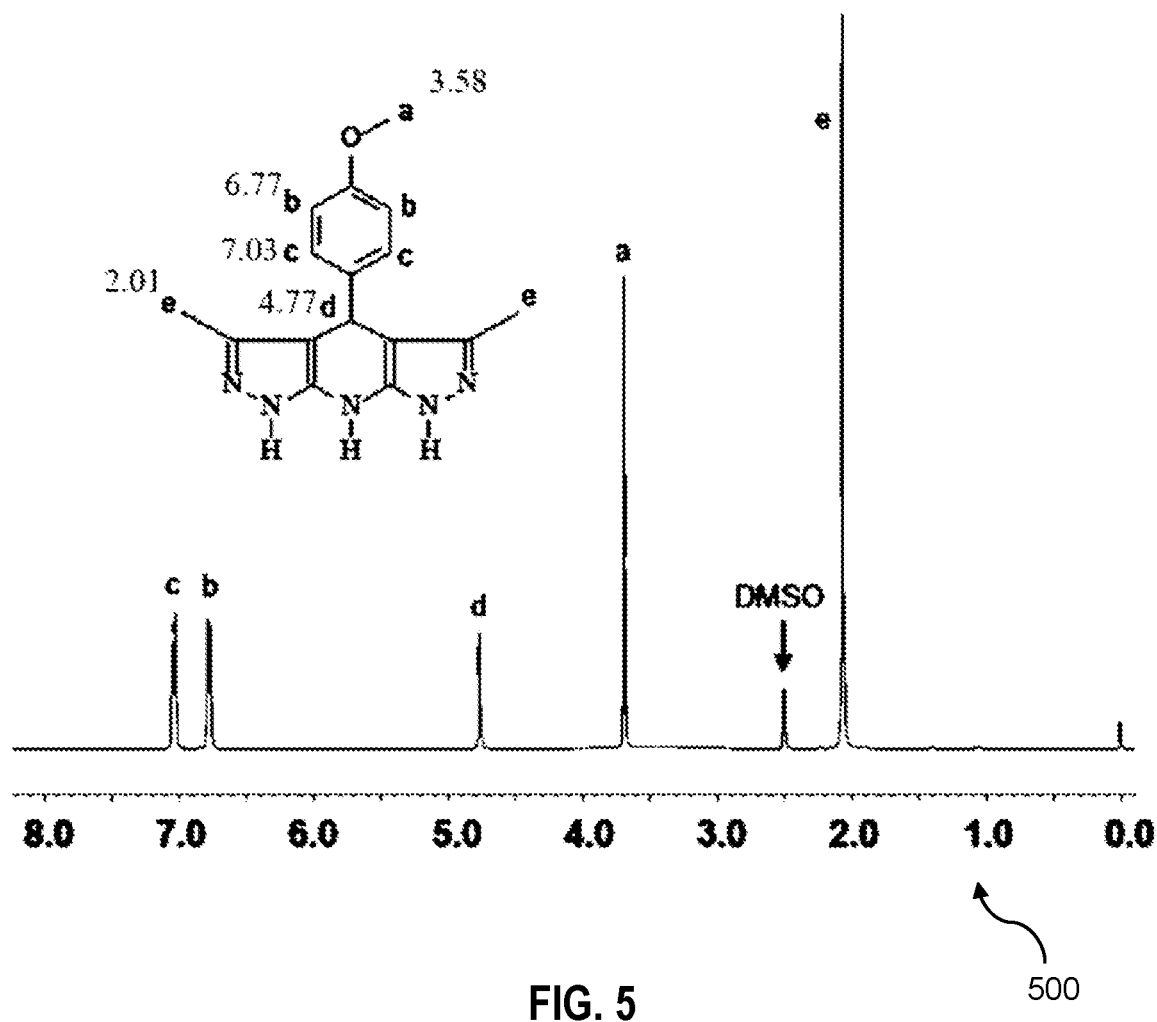
FIG. 5 is a proton nuclear magnetic resonance ($^1$H NMR) spectrum of an example corrosion inhibitor.

FIG. 5 is a proton ($^1$H) NMR spectrum 500 of the corrosion inhibitor (pyrazolopyridine derivative). The peaks are indicated in FIG. 5 and are as follows; $\delta_H$ (DMSO-d$_6$): 2.01 (6H, s), 3.58 (3H, s), 4.77 (1H, s), 6.77 (2H, d), and 7.03 (2H, d).

Figure 6:
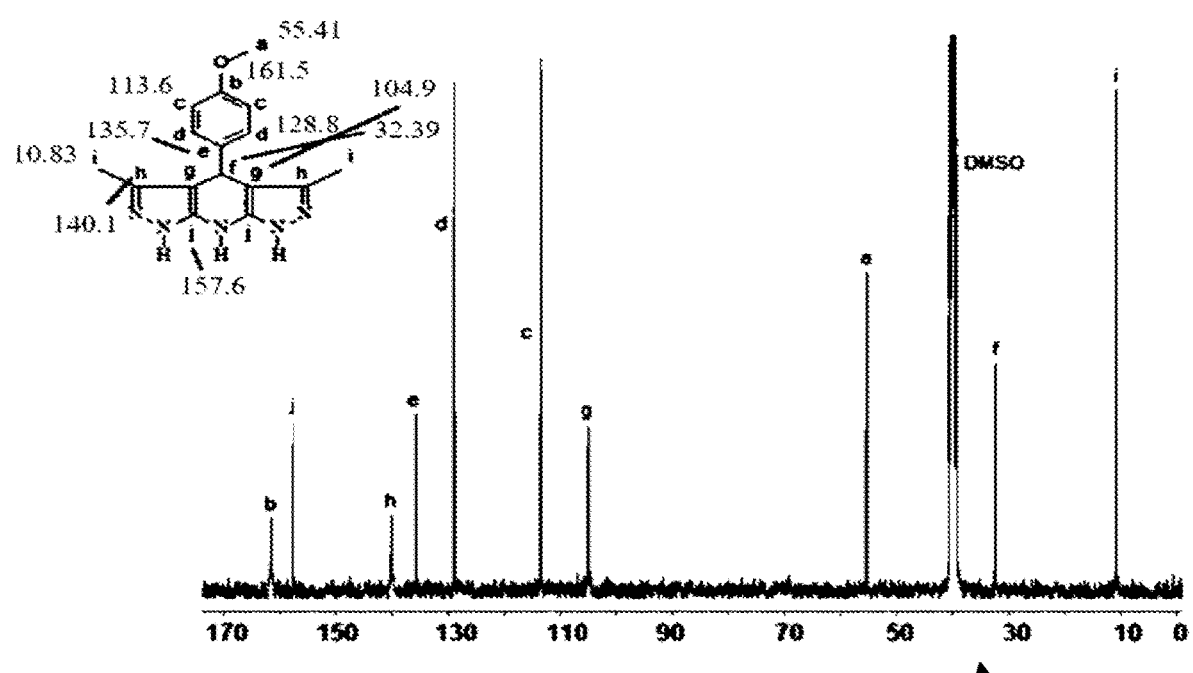
FIG. 6 is a Carbon-13 nuclear magnetic resonance ($^{13}$C NMR) spectrum of an example corrosion inhibitor.

FIG. 6 is a Carbon-13 ($^{13}$C) NMR spectrum 600 of the pyrazolopyridine derivative (corrosion inhibitor). The peaks are indicated in FIG. 6 and are as follows; $\delta_C$ (DMSO-d$_6$): 10.83 (2C), 32.39 (1C), 55.41 (1C), 104.9 (2C), 113.6 (2C), 128.8 (2C), 135.7 (1C), 140.1 (2C), 157.6 (2C), and 161.5 (2C).

Figure 7:
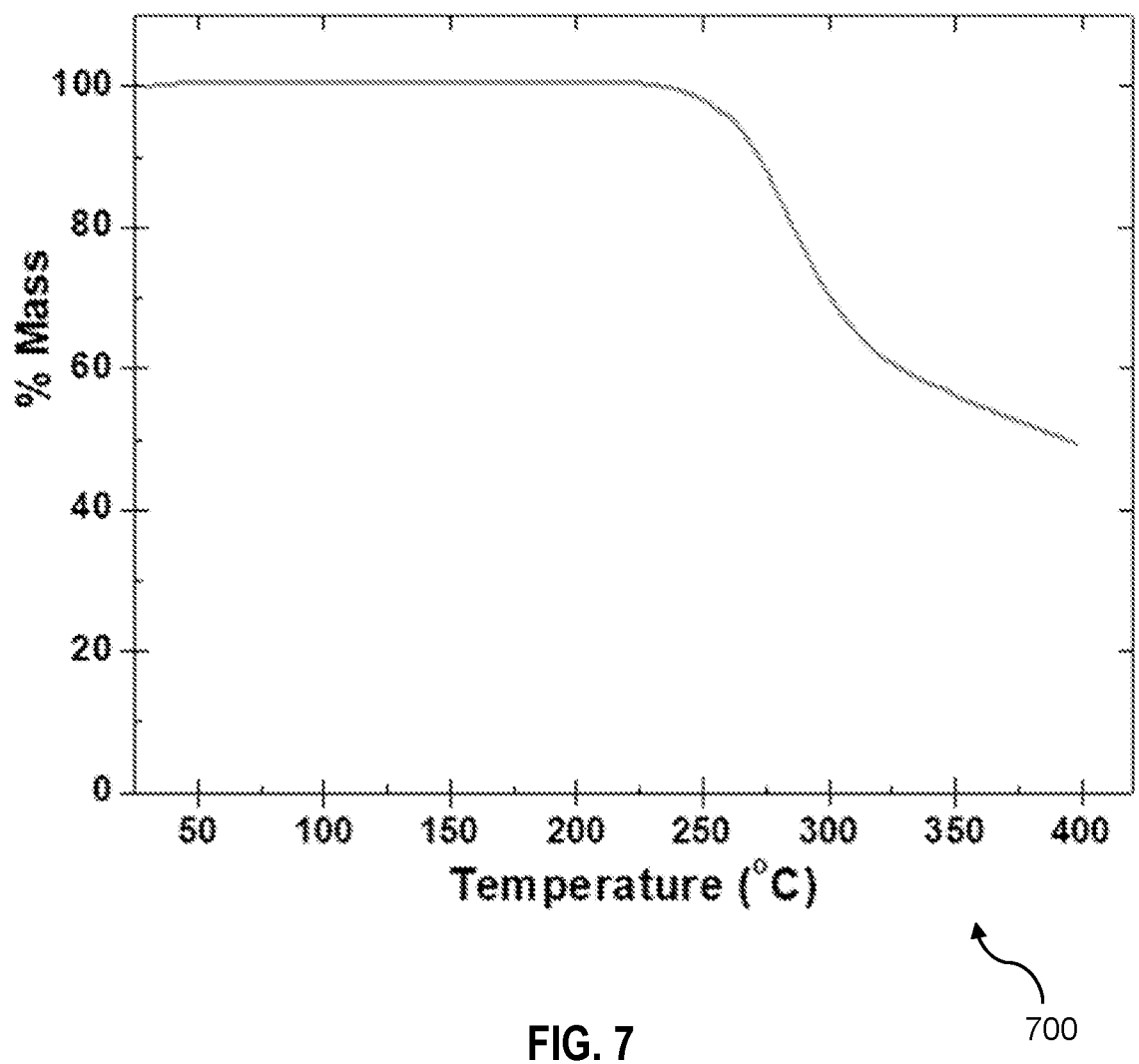
FIG. 7 is a thermal gravimetric analysis (TGA) spectrum of an example corrosion inhibitor.

FIG. 7 is a TGA spectrum 700 of the pyrazolopyridine derivative (corrosion inhibitor). The curve of the TGA spectrum 700 indicates no weight loss in an extended range of temperatures. A steep decline in the weight beyond 240° C. may be linked to the removal of functional groups. Overall, the pyrazolopyridine derivative (corrosion inhibitor) is thermally stable up to about 240° C.

Corrosion Bubble Test

In the bubble test, the performance of the corrosion inhibitor active was tested according to the G3 and G59 ASTM standards. A carbon steel (C-1018) coupon was used for corrosion testing. The test was carried out at 55° C. in a 3.5% sodium chloride (NaCl) solution. Carbon dioxide ($CO_2$) gas was bubbled through the brine solution for the first two hours to de-aerate and was continuously bubbled throughout the experiment to simulate sweet corrosive condition. The solution was continuously stirred at a flow speed of 500 rpm throughout the test. After 2 hours of purging $CO_2$ with gas, the measurement of the corrosion rate of the carbon steel coupon using linear polarization resistance (LPR) was initiated, and the corrosion rate was recorded automatically every 10 minutes. The carbon steel coupon (exposed area of 3.5 square centimeters ($cm^2$)) was subjected to pre-corrosion for 2 hours before injecting the corrosion inhibitor (pyrazolopyridine derivative). A concentration of 100 ppm of the pyrazolopyridine derivative (corrosion inhibitor) was used to evaluate its performance in inhibiting corrosion. The test conditions are provided in Table 1. The test results were then monitored for 24 hours to allow for the corrosion rate to stabilize. The corrosion inhibiting performance was then calculated as percent corrosion protection with respect to the uninhibited baseline corrosion rate ($C_{Ru}$) and the inhibited corrosion rate ($C_{Ri}$) during the 2-hour pre-corrosion period before the addition of the pyrazolopyridine derivative (Equation 1).

$$\% \text{ Corrosion Protection} = \frac{C_{Ru} - C_{Ri}}{C_{Ru}} \times 100\% \quad (1)$$

TABLE 1

Corrosion Bubble Test Conditions

| | |
|---|---|
| Brine Solution | 3.5% NaCl |
| Temperature | 55 ± 2° C. |
| Flow Speed | 500 revolutions per minute (rpm) |
| Test Duration | 24 hours |
| $CO_2$ Purging | 100% |
| Solution pH | 3.8-4.4 |
| Pre-corrosion Duration | 2 hours |
| Corrosion Inhibitor Concentration | 100 ppm |

High Temperature/High Pressure Dynamic Autoclave Test (Weight Loss)

The autoclave test was used to study the performance of the pyrazolopyridine derivative (corrosion inhibitor) at high-temperature, high-pressure, and high-shear stress. A pre-weighed carbon steel (C-1018) coupon was suspended on the head of the autoclave and immersed in 3 liters (L) of 3.5% NaCl test solution. The autoclave was then sealed, de-aerated with nitrogen gas for 1 hour and then pressurized to a pressure of 350 pounds per square inch gauge (psig) (2.4 megapascals (MPa)) with $CO_2$ and heated to 130° C. A flow speed of 1,500 rpm was employed to induce typically high shear stress, and the coupons were exposed for 24 hours. The parameters used for the weight loss test are provided in Table 2. A corrosion inhibitor concentration of 500 ppm was used to evaluate the corrosion inhibiting performance of the pyrazolopyridine derivative under these conditions. After 24 hours, the coupons were removed, cleaned with Super Clark's solution (5 grams per liter (g/L) of N,N-dibutylthiourea dissolved in 18% hydrogen chloride (HCl)), and re-weighed. The corrosion rate in millimeters per year (mm/yr) was calculated according to Equation 2 (ASTM standard: Designation G 1).

$$\text{Corrosion rate (mm/yr)} = \frac{W \times 87{,}600}{A \times T \times D} \quad (2)$$

where W is weight loss in grams (g), A is the exposed surface area in $cm^2$, T is the time of exposure in hours, and D is the density in grams per cubic centimeters ($g/cm^3$) (7.86 $g/cm^3$ for carbon steel).

TABLE 2

Weight Loss Test Conditions

| | |
|---|---|
| Brine Solution | 3.5% NaCl |
| Temperature | 130 ± 2° C. |
| $CO_2$ Partial Pressure | 2.4 MPa (350 psig) |
| Flow Speed | 1500 rpm |
| Test Duration | 24 hours |
| Corrosion Inhibitor Concentration | 500 ppm |

Figure 8:
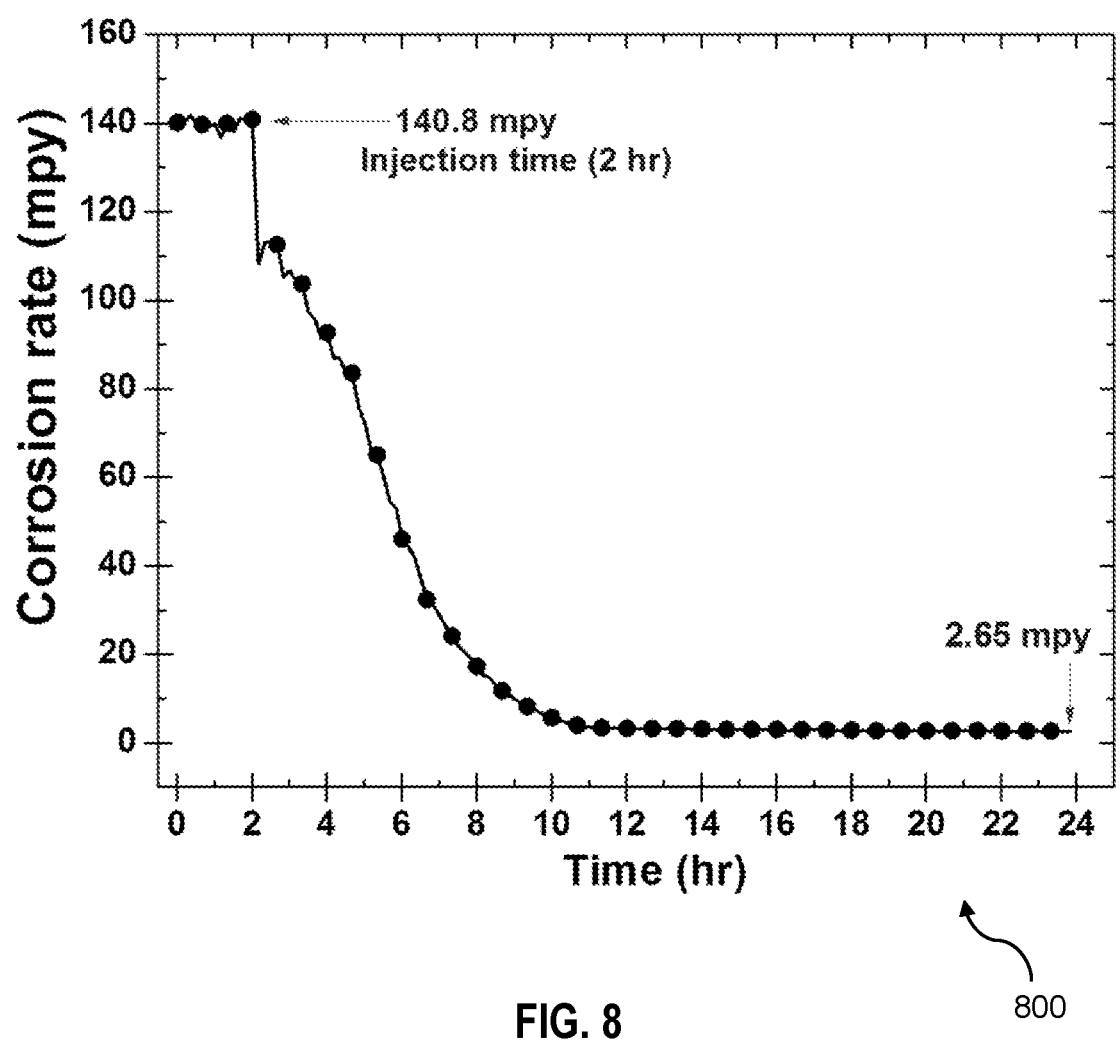
FIG. 8 is a plot of corrosion rate against time for a linear polarization resistance (LPR) test of an example corrosion inhibitor.

FIG. 8 is a plot 800 of corrosion rate against time for a linear polarization resistance (LPR) test on carbon steel coupons over a period of 24 hours with addition of the corrosion inhibitor (pyrazolopyridine derivative). The corrosion inhibitor (pyrazolopyridine derivative) was injected after subjecting the coupons to 2 hours of pre-corrosion. After injecting the corrosion inhibitor (pyrazolopyridine derivative), the corrosion rate of 140.8 mils per year (mpy) of the coupons during pre-corrosion decreased in the presence of the corrosion inhibitor (pyrazolopyridine derivative) to 2.65 mpy after 24 hours, exhibiting a corrosion inhibiting efficiency of 98.12%.

Table 3 shows the corrosion rates and the corresponding corrosion inhibition efficiency. The determination of the weight loss using the weight loss test was conducted for 24 hours. The corrosion rate of the blank (control) was 4667 mpy. For the inhibited active sample with the corrosion inhibitor (pyrazolopyridine derivative), the corrosion rate dropped to 2190 mpy. The corresponding corrosion inhibiting efficiency was 53.08%. The presence of the pyrazolopyridine derivative (corrosion inhibitor) reduces the corrosion rate of steel by more than half at a concentration of 500 ppm under severe conditions, for example, at a temperature of 130° C. (high temperature), a pressure of 350 psig (high pressure), and a flow speed of 1,500 rpm (representing high shear).

TABLE 3

Weight Loss Test Results

| | Corrosion Rate (mpy) | Corrosion Rate (mm/yr) | Corrosion Inhibiting Efficiency (%) |
|---|---|---|---|
| Control | 4,667 | 118.49 | N/A |
| With Corrosion Inhibitor | 2,190 | 55.60 | 53.08 |

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method comprising:
    flowing a composition into a wellbore formed in a subterranean formation, thereby inhibiting corrosion in the wellbore, the composition comprising a pyrazolopyridine derivative comprising:
        a pyridyl moiety;
        a first pyrazole moiety bound to the pyridyl moiety, the first pyrazole moiety comprising an $R_2$ group selected from the group consisting of an alkyl group, a thiol group, a carboxyl group, an aromatic carbonyl group, a hydroxyl group, a methyl amino group, an amide group, and an ester group;
        a second pyrazole moiety bound to the pyridyl moiety, the second pyrazole moiety comprising an $R_3$ group selected from the group consisting of an alkyl group, an amide group, an amino group, a thiol group, a hydroxyl group, an ester group, and a carboxyl group; and
        a phenyl moiety bound to the pyridyl moiety; and
    producing a hydrocarbon from the subterranean formation via the wellbore.

2. The method of claim 1, wherein the pyrazolopyridine derivative has a concentration in the composition in a range of from 100 parts per million (ppm) to 10,000 ppm.

3. The method of claim 2, wherein the phenyl moiety further comprises an $R_1$ group selected from the group consisting of a methoxy group, a carboxyl group, an aromatic amide group, a thiol group, a nitrile group, an azo group, a pyridyl group, a bromophenyl group, and a sulfonic acid group.

4. The method of claim 3, wherein the $R_1$ group is selected from the group consisting of methoxy, mercapto, pyridyl, (bromomethyl)pyridyl, and pyridine-2-aldoxime.

* * * * *